United States Patent
Batzinger et al.

(10) Patent No.: US 6,545,467 B1
(45) Date of Patent: Apr. 8, 2003

(54) CONTOURED SURFACE EDDY CURRENT INSPECTION SYSTEM

(75) Inventors: Thomas James Batzinger, Burnt Hills, NY (US); James Paul Fulton, Clifton Park, NY (US); Curtis Wayne Rose, Mechanicville, NY (US); Lee Cranford Perocchi, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/697,256

(22) Filed: Oct. 27, 2000

(51) Int. Cl.[7] .......................... G01N 27/82; G01N 27/90
(52) U.S. Cl. ......................................... 324/219; 324/242
(58) Field of Search ................................ 324/219–221, 324/238, 241, 242

(56) References Cited

U.S. PATENT DOCUMENTS

| | | | | |
|---|---|---|---|---|
| 4,668,912 A | * | 5/1987 | Junker | 324/220 |
| 5,023,549 A | * | 6/1991 | Dau et al. | 324/220 |
| 5,371,461 A | * | 12/1994 | Hedengren | 324/240 X |
| 5,442,286 A | * | 8/1995 | Sutton, Jr. et al. | 324/219 X |
| 5,465,045 A | * | 11/1995 | Derock | 324/220 |
| 5,659,248 A | | 8/1997 | Hedengren et al. | 324/242 |
| 5,903,147 A | * | 5/1999 | Granger, Jr. et al. | 324/219 |
| 6,114,849 A | * | 9/2000 | Price et al. | 324/219 X |
| 6,339,326 B1 | * | 1/2002 | Trantow | 324/219 |

* cited by examiner

Primary Examiner—Gerard R. Strecker
(74) Attorney, Agent, or Firm—Penny Clarke; Patrick K. Patnode

(57) ABSTRACT

Eddy current inspection of a contoured surface of a workpiece is performed by forming a backing piece of flexible, resiliently yieldable material with a contoured exterior surface conforming in shape to the workpiece contoured surface. The backing piece is preferably cast in place so as to conform to the workpiece contoured surface. A flexible eddy current array probe is attached to the contoured exterior surface of the backing piece such that the probe faces the contoured surface of the workpiece to be inspected when the backing piece is disposed adjacent to the workpiece. The backing piece is then expanded volumetrically by inserting at least one shim into a slot in the backing piece to provide sufficient contact pressure between the probe and the workpiece contoured surface to enable the inspection of the workpiece contoured surface to be performed.

18 Claims, 2 Drawing Sheets

CONTOURED SURFACE EDDY CURRENT INSPECTION SYSTEM

The US Government has a paid-up license in this invention and the right in limited circumstances to require the patent owner to license others on reasonable terms as provided for by the terms of contract number DE-FC21-95MC31176 awarded by the US Department of Energy.

BACKGROUND OF THE INVENTION

This invention relates to nondestructive evaluation of contoured objects such as gas turbine wheel dovetail posts and, more particularly, to a backing piece, an inspection arrangement, and a method for their use in conjunction with eddy current inspection of a contoured surface, such as a gas turbine wheel dovetail post surface.

High performance gas turbine engines typically have a compressor and a turbine which each include a stator and a rotor. The stator is comprised of axially-spaced annular banks having circumferentially arranged, fixed stator vanes. The rotor is comprised of axially-spaced rotatable wheels of circumferentially arranged rotor blades positioned between the annular banks of fixed stator vanes. Each rotor blade typically comprises an outer rotor tip, an air foil and an inner dovetail-shaped base or root which matably mounts within a complementarily-shaped, axial dovetail slot formed between adjacent ones of the dovetail posts on the rim of a rotor wheel. Examples of gas turbine engines include, but are not limited to, gas-turbine power-generation equipment and gas-turbine aircraft engines.

Nondestructive evaluation of gas turbine wheel dovetail posts for the presence of cracks has previously been accomplished by scanning the surface of the dovetail post on either side of the dovetail slot using a single inflexible coil probe. More recently, the instant assignee has developed, a flexible eddy current array probe for use in dovetail post surface inspections in gas turbine aircraft engine parts. The key to using the flexible eddy current array probe is the contact pressure between the probe and the dovetail post surface being inspected. Even or uniform contact pressure must be maintained over the entire area of the flexible eddy current probe during the inspection process.

The dovetail posts employed in gas turbine aircraft engine parts are considerably smaller in dimension when compared to dovetail posts employed in power generation gas turbines. With respect to gas turbine aircraft engines, a pneumatic backing system is used to ensure that the desired contact pressure is provided between the flexible eddy current probe and the inspection surface of the dovetail post. A problem exists, however, in that while this approach works well for the small dovetail posts of gas turbine aircraft engines, it is not efficient for the large dovetail posts used in power generation gas turbine components since the large size of the dovetail posts would require time-consuming multi-passes of the inspection probe during the inspection process.

Consequently, a need exists for an innovation which will provide a solution to the aforementioned problem without introducing any new problems in place thereof.

BRIEF SUMMARY OF THE INVENTION

A contoured surface eddy current inspection backing piece, inspection arrangement, and inspection method are designed to satisfy the aforementioned need. The backing piece, inspection arrangement and inspection method are adapted for effectively carrying out eddy current inspection, generally, of any contoured surface and, more particularly, of the surface of a gas turbine wheel dovetail post of a power generation gas turbine.

In one embodiment of the invention, a backing piece is provided for use in eddy current inspection of a contoured surface, such as a turbine wheel dovetail post surface. The backing piece comprises a body made of a resiliently yieldable material so as to be flexible and capable of expansion in size. The body has at least one contoured exterior surface that conforms in shape to a contoured surface of a workpiece to be inspected. The body further has means therein to facilitate expansion of the body, and to provide sufficient contact pressure between the contoured exterior surface of the body and the contoured surface of the workpiece to enable the contoured surface of the workpiece to be inspected. The body is substantially solid, and made of a material which, for example, can be a castable rubber compound. The expansion facilitating means is an elongated slot formed in the body and open at a location on a side of the body displaced from the contoured exterior surface thereof.

In another embodiment of the invention, an inspection arrangement provides for eddy current inspection of a contoured surface of a workpiece, such as the dovetail post surface of a turbine wheel. The inspection arrangement comprises the flexible and expandable backing piece, as described above, and a flexible eddy current array probe attached to the at least one contoured exterior surface of the backing piece such that the probe faces the contoured surface of the workpiece to be inspected when the backing piece is positioned adjacent to the workpiece. The inspection arrangement further comprises at least one shim insertable into the slot in the backing piece for the purpose of expanding the backing piece in size to provide sufficient contact pressure between the probe and the contoured surface of the workpiece to enable the contoured surface of the workpiece to be inspected when the backing piece is positioned adjacent to the workpiece.

In still another embodiment of the invention, a method is provided for eddy current inspection of a contoured surface of a workpiece, such as the dovetail post surface of a turbine wheel. The inspection method comprises the steps of forming a backing piece of resiliently yieldable material which is flexible and capable of expanding in size and having at least one contoured exterior surface conforming in shape to the contoured surface of the workpiece to be inspected, attaching a flexible eddy current array probe to the at least one contoured exterior surface of the backing piece such that the probe faces the contoured surface of the workpiece to be inspected when the backing piece is disposed adjacent to the workpiece, and expanding the backing piece to provide contact pressure between the probe and the contoured surface of the workpiece to be inspected. Further, the expanding step includes forming a slot in the backing piece so as to be open at a location on a side of the backing piece displaced from the at least one contoured exterior surface of the backing piece, and inserting at least one shim into the slot in the backing piece so as to expand the backing piece in size to provide sufficient contact pressure between the probe and the contoured surface of the workpiece to enable the contoured surface of the workpiece to be inspected.

DETAILED DESCRIPTION OF THE INVENTION

Figure 1:
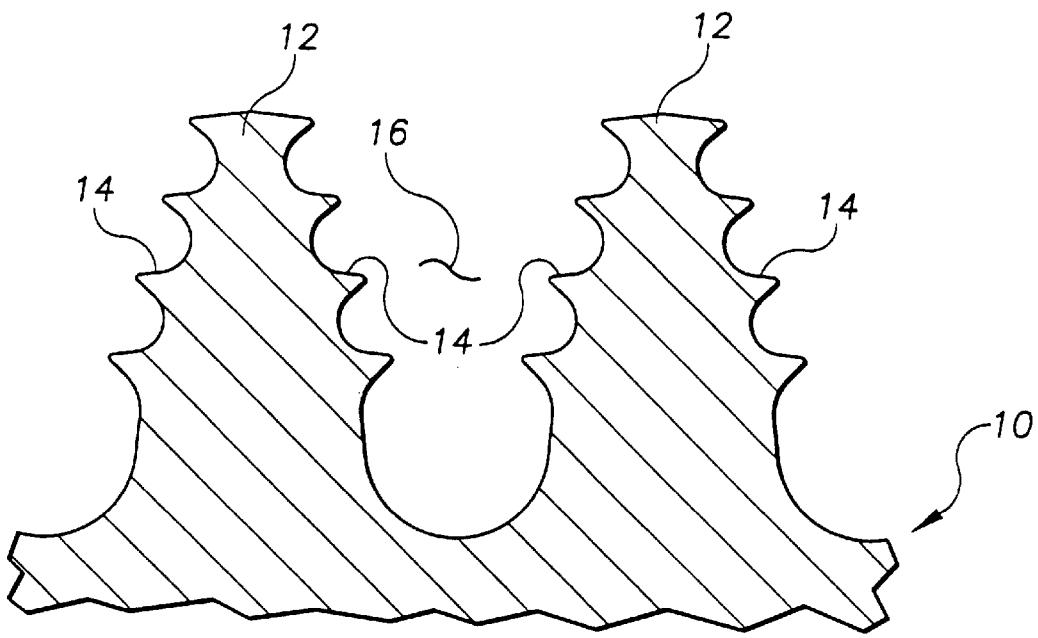
FIG. 1 is an axial sectional view of the rim of a turbine rotor wheel showing a pair of dovetail posts having contoured facing surfaces forming a dovetail slot therebetween to be inspected for the presence of cracks.

FIG. 1 illustrates, in cross section, an annular rim 10 of a turbine rotor wheel having a pair of annular dovetail posts 12 thereon which define dovetail contoured surfaces 14 facing toward one another that form an annular dovetail-shaped slot 16 between them. The dovetail slot is adapted to matably receive complementarily-shaped dovetail roots of rotor blades (not shown) arranged circumferentially about wheel rim 10. Eddy current inspection for presence of cracks in the contoured surfaces of dovetail posts 12 is performed by employing a backing piece 18, shown in FIG. 2, to mount an eddy current array probe 20, as shown in FIG. 3, and is disposed in an inspection arrangement 22, shown in FIG. 4.

Figure 2:
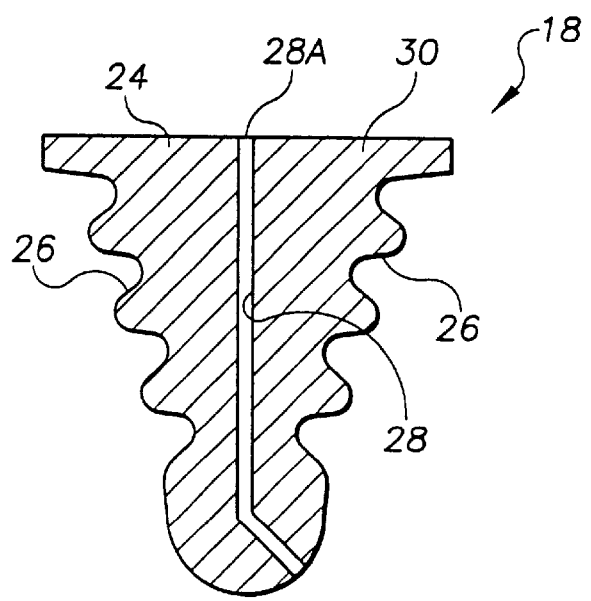
FIG. 2 is a sectional view of a backing piece used in the inspection method of the invention.
Figure 3:
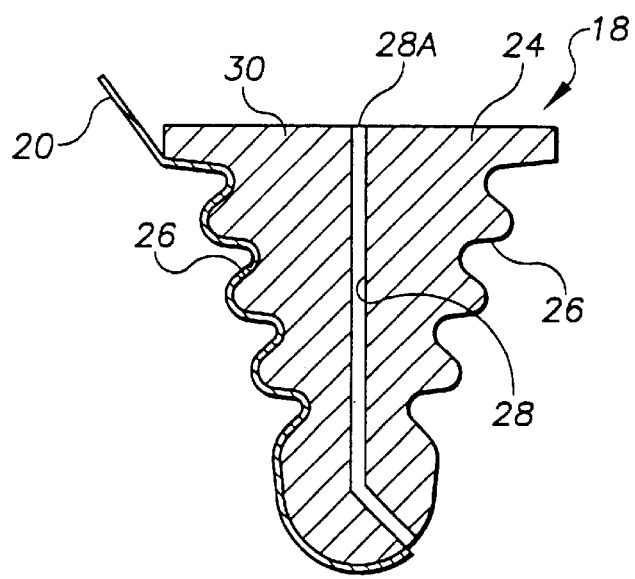
FIG. 3 is a sectional view of the backing piece of FIG. 2 with a flexible eddy current array probe attached thereto for employment in the inspection method of the invention.

FIG. 2 illustrates backing piece 18 used for employment in a preferred embodiment of an inspection system. The backing piece includes a body 24 of a resiliently yieldable or pliant material, such as a castable rubber compound or the like, so as to be flexible and capable of expansion in volumetric size. One suitable material is a casting compound identified as TC-5050 sold by BJB Enterprises, Inc. Body 24, which is substantially solid in configuration, has a pair of contoured exterior surfaces 26 facing in generally opposite directions and conforming in shape to the respective facing contoured surfaces 14 of the adjacent annular dovetail posts to be inspected. Body 24 is thus fittable within dovetail slot 16.

Body 24 further has means in the form of an elongated slot 28 therein for facilitating expansion of body 24 in order to provide a desired level of contact pressure between contoured exterior surfaces 26 of the body and the contoured surfaces 14 of annular dovetail posts 12. Elongated slot 28 is open at one end 28A at a location on a radially exterior surface 30 of body 24 which is displaced from the contoured exterior surfaces of body 24. The radially exterior surface of body 24 extends between and interconnects contoured exterior surfaces 26 thereof.

Body 24 can be fabricated using any suitable technique. One such technique for fabricating body 24 is to cast the body using a test dovetail slot as a mold. The test dovetail slot is also used to verify operation of a broaching tool used in the manufacture of gas turbine dovetail posts. Once the rubber compound cast forming body 24 has cured, flexible eddy current array probe 20 is attached, as shown in FIG. 3, to at least one of the contoured surfaces of body 24 by any suitable means, such as through use of an adhesive tape or the like. Slot 28 is also cast in body 24 during the casting operation.

Figure 4:
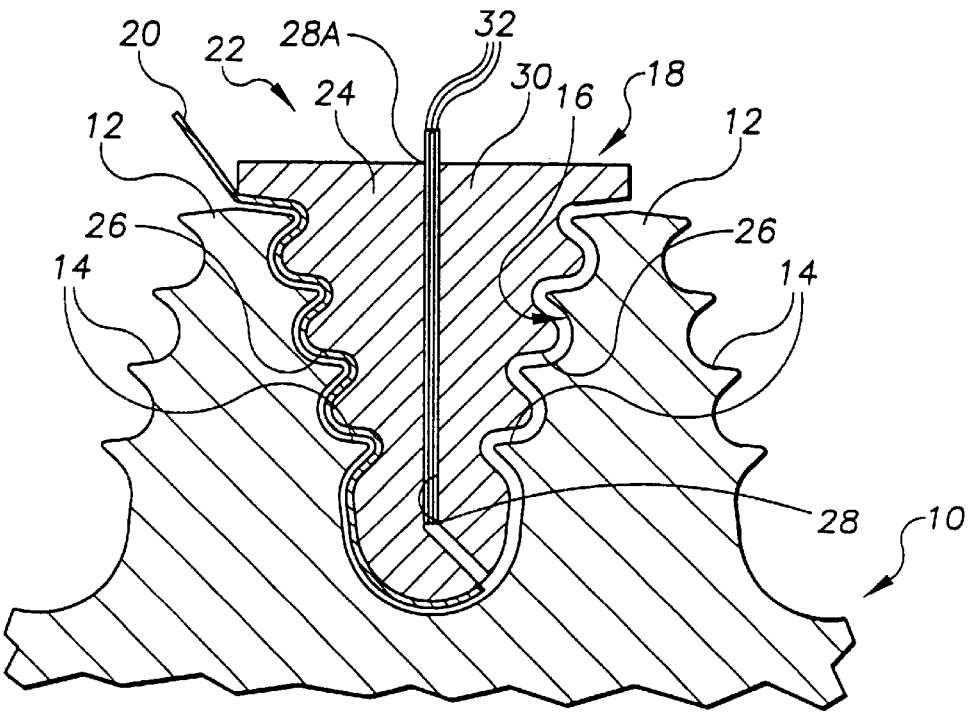
FIG. 4 is a sectional view of the backing piece with the flexible eddy current array probe attached thereto and positioned within the dovetail slot, and shimmed to provide adequate contact pressure between the probe and dovetail post surface to be inspected.

FIG. 4 illustrates inspection arrangement 22 which includes backing piece 18 with flexible eddy current array probe 20 attached thereto, as shown in FIG. 3, and disposed within dovetail slot 16, as shown in FIG. 4. The array is comprised of a plurality of sensors (not shown) embedded within a flexible backing, as disclosed in Hedengren et al. U.S. Pat. No. 5,659,248, issued Aug. 19, 1997 and assigned to the instant assignee. U.S. Pat. No. 5,659,248 is herein incorporated by reference. Inspection arrangement 22 also includes one or more shims 32 which are inserted into slot 28 in backing piece 18 in order to expand the size of the backing piece so as to provide the desired level of contact pressure between probe 20 and the respective one of contoured surfaces 14 of dovetail post 12 which is faced by, and to be inspected in a known manner by, probe 20. The desired level of contact pressure is attained when there is intimate contact with the sources being inspected across the entire array of the probe, and preferably should not be raised above that level.

The method for providing eddy current inspection of a contoured surface, such as the turbine wheel dovetail post surface 14, thus includes the steps of forming, such as by casting, the body of backing piece 18 of resiliently yieldable material which is flexible and capable of expansion in size. Body 24 has at least one contoured exterior surface 26 conforming in shape to the contoured surfaces of dovetail posts 12 to be inspected. Flexible eddy current array probe 20 is attached to at least one of the contoured exterior surfaces of body 24 such that the probe faces the contoured surface of dovetail post 12 to be inspected. Body 24 is expanded by inserting shims 32 into slot 28 to provide contact pressure between the probe and contoured surface 14 of post 12 sufficient to perform the eddy current inspection.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A backing piece for attaching to a flexible eddy current array probe for eddy current inspection of a contoured surface, comprising:

a body consisting of a flexible, resiliently yieldable material;

said body having at least one contoured exterior surface conforming in shape to a contoured surface of a workpiece to be inspected;

said body further having means therein for facilitating volumetric expansion of said body so as to provide sufficient contact pressure between said contoured exterior surface of said body and the contoured surface of the workpiece to enable the contoured surface of the workpiece to be inspected when the body is disposed adjacent to the workpiece;

said body being substantially solid and substantially extending between the contoured surface and an opposing surface of the workpiece.

2. The backing piece of claim 1 wherein said material comprises a castable rubber compound.

3. The backing piece of claim 1, wherein the expansion facilitating means comprises an elongated slot in said body, said elongated slot being open at a location on a radially exterior surface of said body, the location being displaced from said contoured exterior surface of said body.

4. A backing piece for attaching to a flexible eddy current array probe for eddy current inspection of a turbine wheel dovetail post contoured surface, comprising:

a body consisting of a flexible, resiliently yieldable material;

said body being substantially solid and having a pair of contoured exterior surfaces facing in generally opposite directions and conforming in shape to respective facing contoured surfaces of a pair of annular dovetail posts of a turbine rotor wheel;

said body further being fittable within a dovetail slot defined by, and substantially extending between, the respective facing contoured surfaces of the annular dovetail posts;

said body further having means therein for facilitating volumetric expansion to provide sufficient contact pressure between said contoured exterior surfaces of said body and the contoured surfaces of the dovetail posts to enable the contoured surfaces of the dovetail posts to be inspected when said body is fitted within the dovetail slot between the dovetail posts.

5. The backing piece of claim 4 wherein said material comprises a castable rubber compound.

6. The backing piece of claim 4, wherein the expansion facilitating means comprises an elongated slot in said body, said elongated slot being open at a location on a radially external surface of said body, the location being displaced from said contoured exterior surfaces of said body.

7. An inspection arrangement for eddy current inspection of a contoured surface of a workpiece, comprising:

a backing piece consisting of a flexible, resiliently yieldable material and having at least one contoured exterior surface conforming in shape to the contoured surface of the workpiece to be inspected, said backing piece further having means therein for facilitating volumetric expansion of said backing piece to provide sufficient contact pressure between said contoured exterior surface of said backing piece and the contoured surface of the workpiece to enable the contoured surface of the workpiece when the backing piece is disposed adjacent to the workpiece, and said backing piece being substantially solid and substantially extending between the contoured surface and an opposing surface of the workpiece; and a flexible eddy current array probe attached to said at least one contoured exterior surface of said backing piece such that said probe faces said contoured surface of the workpiece when said backing piece is disposed adjacent to the workpiece.

8. The inspection arrangement of claim 7, wherein the expansion facilitating means comprises an elongated slot in said backing piece, said elongated slot being open at a location on a radially external surface of said backing piece, said location being displaced from said contoured exterior surface of the backing piece.

9. The inspection arrangement of claim 8 further comprising:

at least one shim insertable into said slot in said backing piece so as to expand said backing piece in size to provide adequate contact pressure between said probe and the contoured surface of the workpiece to enable the contoured surface of the workpiece to be inspected when said backing piece is disposed adjacent to the workpiece.

10. An inspection arrangement for eddy current inspection of a turbine wheel dovetail post contoured surface, comprising:

a backing piece consisting of a flexible, resiliently yieldable material, being substantially solid, and having a pair of contoured exterior surfaces facing in generally opposite directions and conforming in shape to respective facing contoured surfaces of a pair of annular dovetail posts of a turbine rotor wheel, said backing piece further being fittable within a dovetail slot defined by, and substantially extending between, the respective facing contoured surfaces of the annular dovetail posts; and a flexible eddy current array probe attached to one of said contoured exterior surfaces of said backing piece and facing one of said contoured surfaces to be inspected when said backing piece is fitted within the dovetail slot between the dovetail posts, said backing piece further having means therein for facilitating expansion of said backing piece when said backing piece is fitted within the dovetail slot to provide sufficient contact pressure between said probe and the one of the contoured surfaces to be inspected to enable the one of the contoured surfaces to be inspected.

11. The inspection arrangement of claim 10, wherein the expansion facilitating means comprises an elongated slot in said backing piece, said elongated slot being open at a location on a radially external surface of said backing piece, the location being displaced from said contoured exterior surfaces of the backing piece.

12. The inspection arrangement of claim 11 further comprising:

at least one shim insertable into said slot in said backing piece so as to expand said backing piece in size to provide adequate contact pressure between said probe and the one of the contoured surfaces of the dovetail posts to enable the one of the contoured surfaces to be inspected.

13. A method for eddy current inspection of a contoured surface of a workpiece, comprising:

forming a backing piece consisting of a flexible, resiliently yieldable material with a contoured exterior surface conforming in shape to a contoured surface of the workpiece, wherein the backing piece is substantially solid;

attaching a flexible eddy current array probe to the contoured exterior surface of the backing piece;

positioning the backing piece and probe in an opening within the workpiece, the opening being defined by the contoured surface and an opposing surface of the workpiece, such that the probe faces the contoured surface of the workpiece and the backing piece substantially extends from the contoured surface to the opposing surface of the workpiece; and expanding the backing piece to provide sufficient contact pressure between the probe and the contoured surface of the workpiece to enable the contoured surface of the workpiece to be inspected.

14. The method of claim 13 wherein the sufficient contact pressure is at a level resulting in intimate contact with the workpiece over the entire array of the probe.

15. The method of claim 13, wherein said expansion includes:

forming a slot in the backing piece, said slot being open at a location on a radially exterior surface of the backing piece, the location being displaced from said contoured exterior surface of the backing piece; and inserting at least one shim into the slot in the backing piece so as to expand the backing piece in size to provide said sufficient contact pressure between the probe and the contoured surface of the workpiece to be inspected.

16. A method for eddy current inspection of a turbine rotor wheel dovetail post contoured surface, comprising:

casting a backing piece consisting of a flexible, resiliently yieldable material in a configuration having a pair of contoured exterior surfaces facing in generally opposite directions and conforming in shape to respective facing contoured surfaces of a pair of annular dovetail posts of said turbine rotor wheel, wherein said backing piece is substantially solid and substantially extends between the facing contoured surfaces of the pair of annular dovetail posts;

attaching a flexible eddy current array probe to one of the contoured exterior surfaces of the backing piece;

fitting the backing piece within a dovetail slot defined by, and situated between, the respective facing contoured surfaces of the annular dovetail posts such that the probe on said one of the contoured exterior surface of the backing piece faces one of the respective facing contoured surfaces of the annular dovetail posts; and expanding the backing piece volumetrically to provide sufficient contact pressure between the probe and said one of said contoured surfaces of the annular dovetail posts to be inspected to enable said one of said contoured surfaces to be inspected.

17. The method of claim 16 wherein the sufficient contact pressure is at a level resulting in intimate contact with said one of said contoured surfaces to be inspected.

18. The method of claim 16 wherein said casting further includes:

casting a slot in the backing piece, said slot being open at a location on a radially exterior surface of the backing piece, the location being displaced from the contoured exterior surfaces of the backing piece;

and wherein the method further includes:

inserting at least one shim into the slot in the backing piece so as to expand the backing piece in size to provide said sufficient contact pressure between said probe and the respective one of the contoured surfaces of the annular dovetail posts to be inspected.

* * * * *